United States Patent
Choi et al.

(10) Patent No.: US 7,976,484 B2
(45) Date of Patent: Jul. 12, 2011

(54) HYPERTHERMO-THERAPEUTIC APPARATUS FOR TREATING LOWER PART OF THE USER'S BODY

(75) Inventors: Byung Won Choi, Chunsan-si (KR);
Hyun Sik Chung, Kyunggi-do (KR);
Keun young Paek, Kimje-si (KR)

(73) Assignee: Ceragem Co. Ltd., Chunan-Si (KR)

( * ) Notice: Subject to any disclaimer, the term of this patent is extended or adjusted under 35 U.S.C. 154(b) by 1244 days.

(21) Appl. No.: 11/566,918

(22) Filed: Dec. 5, 2006

(65) Prior Publication Data

US 2007/0239237 A1    Oct. 11, 2007

(30) Foreign Application Priority Data

Apr. 11, 2006   (KR) .................. 10-2006-0032909

(51) Int. Cl.
*A61F 7/00* (2006.01)
(52) U.S. Cl. .............. 601/15; 607/96; 607/98
(58) Field of Classification Search .......... 607/96, 607/98, 99, 100, 108, 112; 601/15, 18; 606/204, 606/237–245
See application file for complete search history.

(56) References Cited

U.S. PATENT DOCUMENTS

| 6,454,732 | B1 | 9/2002 | Lee et al. | |
| 2002/0058973 | A1* | 5/2002 | Lee | 607/96 |
| 2004/0082983 | A1* | 4/2004 | Park | 607/96 |

FOREIGN PATENT DOCUMENTS

| KR | 10-0159994 | 7/1997 |
| KR | 10-0351476 | 5/2000 |
| KR | 20-0182021 | 5/2000 |
| KR | 20-0197733 | 9/2000 |
| KR | 20030089266 | 11/2003 |

OTHER PUBLICATIONS

English Language Abstract of KR 10-0159994.
English Language Abstract of KR 20-0182021.
English Language Abstract of KR 10-0351476.
English Language Abstract of KR 20-0197733.

* cited by examiner

*Primary Examiner* — Quang D Thanh
(74) *Attorney, Agent, or Firm* — Greenblum & Bernstein P.L.C.

(57) ABSTRACT

An auxiliary mat for a hyperthermo-therapeutic apparatus, a hyperthermo-therapeutic apparatus including the same, and a method of using the hyperthermo-therapeutic apparatus are provided. In a hyperthermo-therapeutic apparatus including a main mat and an auxiliary mat, a receiving groove is formed at a side of the main mat or the auxiliary mat, and an external hyperthermo-therapeutic unit is detachably mounted in the receiving groove. In a state where a user sits astraddle on the main mat or the auxiliary mat, the external hyperthermo-therapeutic unit is operated so that a hot compress effect or an effect generated by radiating far infrared rays can be simply obtained on a lower part of a user's body. Upon use of the hyperthermo-therapeutic apparatus, there are advantages in that the user does not need to take an uncomfortable posture for receiving a hot compress on the lower part of her/his body.

19 Claims, 7 Drawing Sheets

FIG 5

```
Step of mounting external hyperthermo-
therapeutic unit
```
↓

```
Step of sitting astaddle on mat
```
↓

```
Step of obtaining hot compress effect
```

US 7,976,484 B2

HYPERTHERMO-THERAPEUTIC APPARATUS FOR TREATING LOWER PART OF THE USER'S BODY

TECHNICAL FIELD

The present invention relates to an auxiliary mat for a hyperthermo-therapeutic apparatus, a hyperthermo-therapeutic apparatus comprising the same, and a method of using the hyperthermo-therapeutic apparatus, and more particularly, to an auxiliary mat for a hyperthermo-therapeutic apparatus which can more effectively achieve a hot compress effect and an acupressure effect generated by radiating far infrared rays on a crotch region of a lower part of a user's body, a hyperthermo-therapeutic apparatus comprising the same, and a method of using the hyperthermo-therapeutic apparatus.

BACKGROUND ART

Generally, a bed type hyperthermo-therapeutic apparatus has a bed type frame as a basic structure, a main mat mounted on the bed type frame to perform a hot compress for an upper part of a user's body, and an auxiliary mat mounted on the bed type frame to perform a hot compress for a lower part of the user's body, so that the user can obtain a hot compress effect, an acupressure effect and an effect obtained by radiating far infrared rays in a state where the user lies on the main and auxiliary mats. At this time, the bed type hyperthermo-therapeutic apparatus has a certain hyperthermo-therapeutic unit mounted in the main mat, and the hyperthermo-therapeutic unit can be reciprocated inside the main mat by a motor so that the user's vertebral regions including cervical and lumbar vertebrae can be treated intensively by the hyperthermo-therapeutic unit located below the user in the state where the user lies on the main mat. Typical bed type hyperthermo-therapeutic apparatuses include those disclosed in a plurality of patent applications including Korean Patent Application No. 1995-47266, Korean Utility Model Application No. 1999-26999, Korean Patent Application No. 2000-7031, and Korean Utility Model Application No. 2000-11259.

FIG. 1 is a representative view showing a conventional bed type hyperthermo-therapeutic apparatus. Such a bed type hyperthermo-therapeutic apparatus has an advantage in that the user's vertebral regions are automatically treated according to a program stored in a control box in a state where the user lies on the bed type hyperthermo-therapeutic apparatus. Thus, the bed type hyperthermo-therapeutic apparatus is most widely used in these days and has been continuously improved to be adapted to treatment of the user's vertebral regions.

To this end, the conventional bed type hyperthermo-therapeutic apparatus employs curved rails 22 having a shape conforming to those of the user's vertebral regions, instead of linear rails. A hyperthermo-therapeutic unit 10 has been improved to be smoothly moved in an upward/downward direction. As the curved rails 22 are employed, a technique capable of preventing or correcting expansion of a feeding belt 22 coupled with the hyperthermo-therapeutic unit to move the hyperthermo-therapeutic unit has been also improved.

Further, as for the treatment of the user's vertebral regions by the conventional bed type hyperthermo-therapeutic apparatus, new techniques have appeared for controlling the reciprocation of the hyperthermo-therapeutic unit in a mat 21 in an automatic manner, at predetermined time intervals according to a program stored in a controller, or based on an actual moving distance of the hyperthermo-therapeutic unit 10 in the mat 21.

Meanwhile, since the conventional bed type hyperthermo-therapeutic apparatus is utilized for intensively treating the user's vertebral regions including his/her back in the state where the user lies on the mat, an additional external hyperthermo-therapeutic unit is employed for treating other regions including the user's abdomen. The external hyperthermo-therapeutic unit essentially comprises a heat-generating section provided therein for generating heat at high temperature; a circular cap externally wrapping the heat-generating section and receiving the heat generated from the heat-generating section to radiate far infrared rays; and a body section for housing or containing the above components. The heat-generating section is supplied with external electrical energy through an electrical wire.

In a case where a user wants to obtain a hot compress effect and an effect generated by radiating far infrared rays on other regions except his/her back using the conventional bed type hyperthermo-therapeutic apparatus constructed as above, the user grasps the external hyperthermo-therapeutic unit and puts it on his/her abdomen or close to his/her shoulder region so as to treat that region for a certain period of time in a state where the user lies on the mat. Conventionally, as for the external hyperthermo-therapeutic unit, a 3-member hyperthermo-therapeutic unit having three hyperthermo-therapeutic members, a 5-member hyperthermo-therapeutic unit having five hyperthermo-therapeutic members and a 9-member hyperthermo-therapeutic unit having nine hyperthermo-therapeutic members are mainly used.

When the user wants to use the external hyperthermo-therapeutic unit, however, the user should grasp the body section of the external hyperthermo-therapeutic unit and move it to a region of his/her body to be treated. Thus, there may be occasionally a region where it is difficult to use the external hyperthermo-therapeutic unit. For example, this region is a crotch region of a lower part of the user's body, which is the region for treating the prostate in case of a man and the region including the uterus for treating and preventing woman's diseases in case of a woman.

When the user utilizes the conventional bed type hyperthermo-therapeutic apparatus by grasping the external hyperthermo-therapeutic unit and moving it to his/her crotch region, it is difficult for the user to perform a hot compress and a far infrared ray radiating treatment in this state and other accompanying people consider the above treatment action as an unnatural and unpleasant action if the user is with others. Accordingly, in the case where the user utilizes the conventional bed type hyperthermo-therapeutic apparatus, there is a disadvantage in that the user cannot help abandoning the treatment for such regions.

Consequently, even though the user wants to treat a lower part of his/her body or perform a therapeutic and preventive action, there has not been provided a proper method of using the hyperthermo-therapeutic apparatus. Therefore, the conventional bed type hyperthermo-therapeutic apparatus has a disadvantage in that it is substantially difficult to achieve a treatment effect on the user's crotch region.

DISCLOSURE OF INVENTION

Technical Problem

As described above, the conventional bed type hyperthermo-therapeutic apparatus has a disadvantage in that a user cannot effectively and simply obtain a hot compress effect and an effect generated by radiating far infrared rays on a crotch region of his/her body due to current essential and structural limitations on the hyperthermo-therapeutic apparatus.

Accordingly, an object of the present invention is to provide an auxiliary mat for a hyperthermo-therapeutic apparatus and a hyperthermo-therapeutic apparatus comprising the same, wherein a user can easily and simply obtain a hot compress effect and an effect generated by radiating far infrared rays on a crotch region of the user's body while obtaining the function and performance of a conventional hyperthermo-therapeutic apparatus as they are.

Another object of the present invention is to provide a method of using the hyperthermo-therapeutic apparatus which allows a user to easily and simply obtain a hot compress effect and an effect generated by radiating far infrared rays on a crotch region of the user's body while obtaining the function and performance of a conventional hyperthermo-therapeutic apparatus as they are.

Technical Solution

The present invention relates to an auxiliary mat for a hyperthermo-therapeutic apparatus and a hyperthermo-therapeutic apparatus comprising the same, wherein a user can more effectively obtain a hot compress effect and an effect generated by radiating far infrared rays on a crotch region of a lower part of a user's body.

In a hyperthermo-therapeutic apparatus including a main mat for use in giving a hot compress effect to an upper part of a user's body and an auxiliary mat for use in giving a hot compress effect to a lower part of the user's body according to the present invention, the auxiliary mat comprises a receiving groove formed at a side of a body thereof, an external hyperthermo-therapeutic unit detachably or slidably mounted in the receiving groove; and a hyperthermo-therapeutic unit cover coupled above the external hyperthermo-therapeutic unit while outwardly exposing a hyperthermo-therapeutic member of the external hyperthermo-therapeutic unit.

In the present invention, the auxiliary mat may comprise a cover for wrapping the body of the auxiliary mat. It is preferred that the cover allow a hyperthermo-therapeutic member, which has been exposed outside the hyperthermo-therapeutic unit cover, to be exposed therethrough.

In the present invention, the auxiliary mat may further comprise a heat-generating means provided inside with respect to the receiving groove to generate heat by using externally supplied electric energy; and a precious stone plate lying on the heat-generating means and radiating far infrared rays by means of the heat generated by the heat-generating means.

In the present invention, it is more preferred that the precious stone plate comprise a plurality of platelets. More specifically, the precious stone plate preferably comprises 2~12 platelets.

In the present invention, if the main mat and the auxiliary mat are mounted on a frame body, the hyperthermo-therapeutic apparatus can be converted into a bed type hyperthermo-therapeutic apparatus.

The present invention provides a method of using a hyperthermo-therapeutic apparatus including a main mat for use in giving a hot compress effect to an upper part of a user's body and an auxiliary mat for use in giving a hot compress effect to a lower part of the user's body comprising the steps of: mounting, by a user, an external hyperthermo-therapeutic unit in a receiving groove formed at a side of the auxiliary mat; sitting astraddle, by the user, on an upper side of the external hyperthermo-therapeutic unit mounted in the receiving groove; and operating, by the user, the external hyperthermo-therapeutic unit to obtain a hot compress effect.

Advantageous Effects

As described above, since an additional receiving groove is formed in the main mat or the auxiliary mat and the external hyperthermo-therapeutic unit is mounted in the receiving groove in the hyperthermo-therapeutic apparatus according to the present invention, a user can simply sit astraddle on an upper side of the external hyperthermo-therapeutic unit and enables the hyperthermo-therapeutic member to be placed directly at a lower part of his/her body in this state.

Thus, upon use of the hyperthermo-therapeutic apparatus of the present invention, there is an advantage in that the user can operate the external hyperthermo-therapeutic unit in such a state and directly obtain a hot compress effect and an effect generated by radiating far infrared rays on the lower part of his/her body.

Further, upon use of the hyperthermo-therapeutic apparatus of the present invention, the user can utilize the hyperthermo-therapeutic apparatus while freely selecting a region of his/her body to be treated. Thus, there are advantages in that the present invention can be advantageously utilized for preventing diseases related to the prostate of a man as well as for preventing various diseases of women including women's diseases.

Moreover, upon use of the hyperthermo-therapeutic apparatus of the present invention, there are advantages in that it is sufficient for the user to only correct her/his sitting posture without needing to grasp the external hyperthermo-therapeutic unit and to put the external hyperthermo-therapeutic unit at a lower part of his/her own body or to squat down on the external hyperthermo-therapeutic unit, and thus, the user can simply give a hot compress effect to the lower part of his/her own body without any burden. Since this posture merely appears to be a figure in which the user naturally sits astraddle on a bed or mat, there is an advantage in that even though there are other people around the user, the user can conveniently utilize the hyperthermo-therapeutic apparatus.

BRIEF DESCRIPTION OF DRAWINGS

FIG. 5 is a block diagram illustrating respective steps of a method of using the hyperthermo-therapeutic apparatus 100 according to the present invention.

BEST MODE FOR CARRYING OUT THE INVENTION

Figure 1:
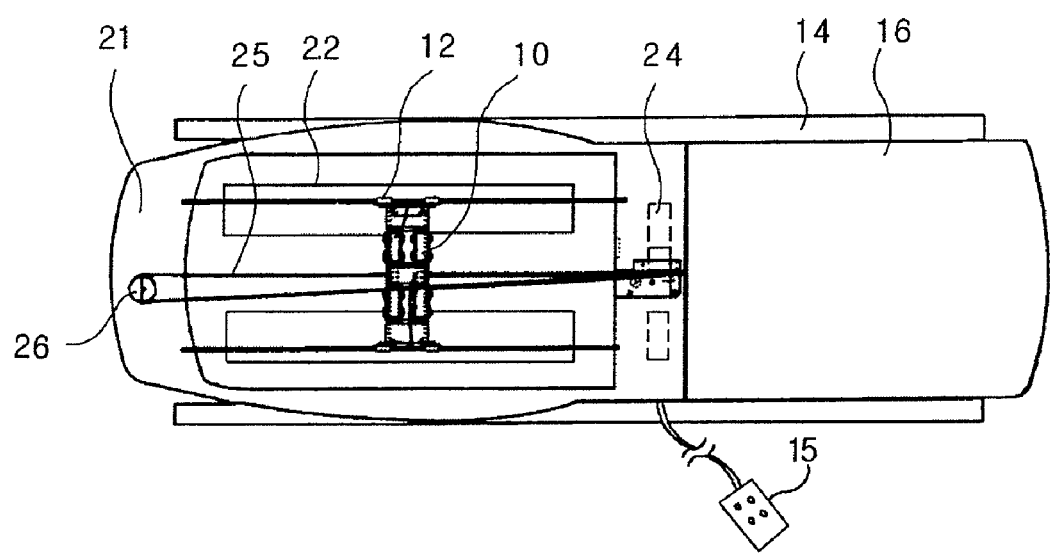
FIG. 1 is a representative view showing a conventional hyperthermo-therapeutic apparatus.

Hereinafter, the present invention will be described in greater detail with reference to accompanying drawings.

However, it will be apparent that the accompanying drawings only illustrate the technical sprit of the present invention and the technical spirit of the present invention is not limited thereto.

The present invention provides a hyperthermo-therapeutic apparatus 100 essentially comprising a main mat 110 for use in giving a hot compress effect to an upper part of a user's body, and an auxiliary mat 120 for use in giving a hot compress effect to a lower part of the user's body. The hyperthermo-therapeutic apparatus comprising the main mat 110 and the auxiliary mat 120 can be called "a mat type hyperthermo-therapeutic apparatus," whereas a hyperthermo-therapeutic apparatus constructed by mounting the main mat 110 and the auxiliary mat 120 on a frame body 130 can be called "a bed type hyperthermo-therapeutic apparatus."

In the present invention, the hyperthermo-therapeutic apparatus 100 includes all the mat type and bed type hyperthermo-therapeutic apparatuses each of which can be considered as one of preferred embodiments of the hyperthermo-therapeutic apparatus according to the present invention.

For the sake of convenience of description, the present invention will be described in connection with the bed type hyperthermo-therapeutic apparatus that has been most popularized in these days. However, it will be readily understood by those skilled in the art that the following description is only for illustrative purposes.

In the present invention, a main mat 110 contains a hyperthermo-therapeutic unit 10, which is reciprocated therein, so that a hot compress can be performed on user's vertebral regions by the hyperthermo-therapeutic unit; and a motor 24 for reciprocating the hyperthermo-therapeutic unit. On the other hand, the auxiliary mat 120 is provided for performing a hot compress on a lower part of the user's body, and may contain an additional hyperthermo-therapeutic unit (not shown) and a motor (not shown) therein.

The hyperthermo-therapeutic apparatus 100 of the present invention comprises a receiving groove 140 formed at a side of the auxiliary mat 120. Although it is preferred that the receiving groove 140 be formed at a side of the auxiliary mat 120, the receiving groove may be provided in an additional space section of the main mat 110, if present. The drawings of the present application exemplarily show that the receiving groove is formed in the auxiliary mat 120. This is because a larger marginal space can be secured in the auxiliary mat 120 as compared with the main mat 110.

Figure 2:
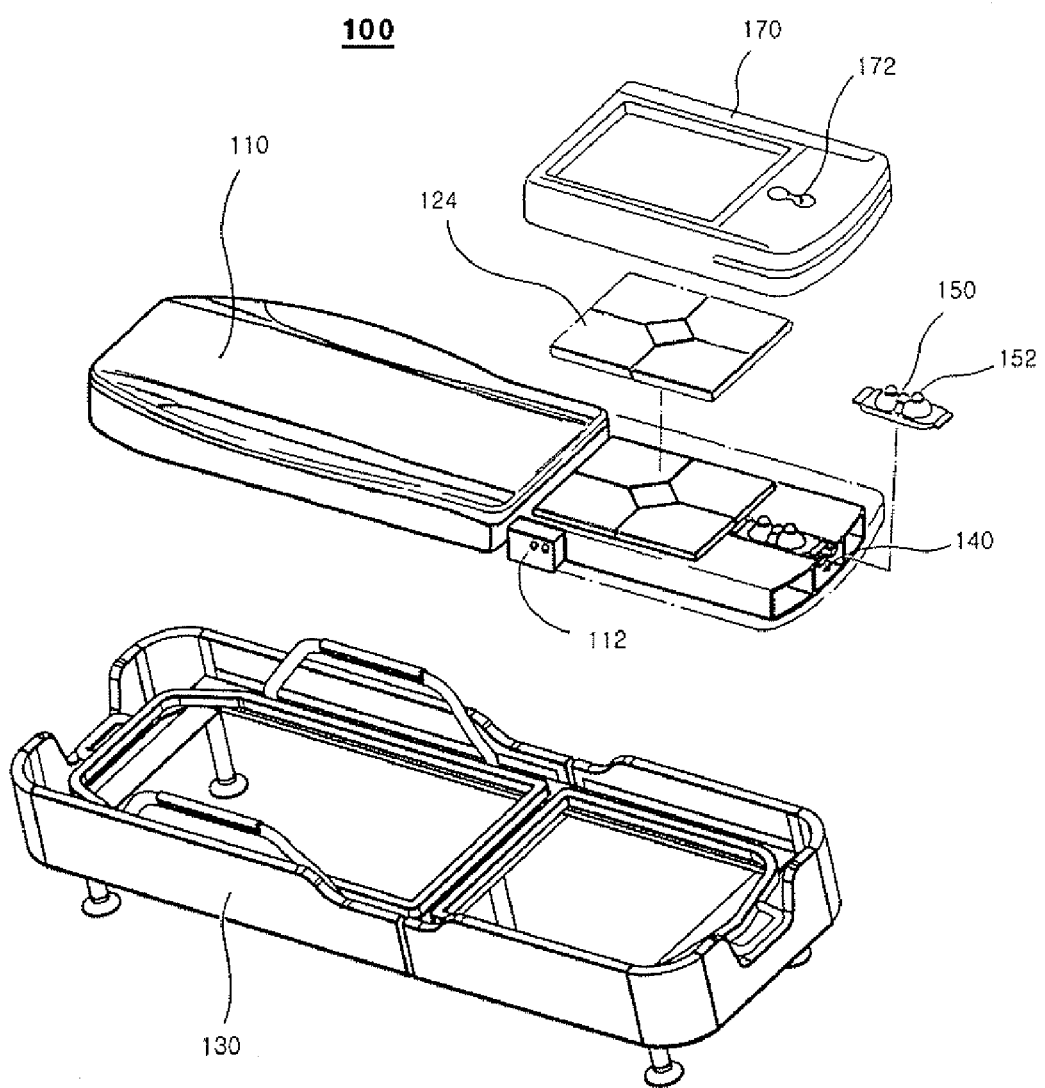
FIG. 2 is an exploded perspective view of components of a bed type hyperthermo-therapeutic apparatus selected as an example of a preferred embodiment of the present invention.
Figure 3:
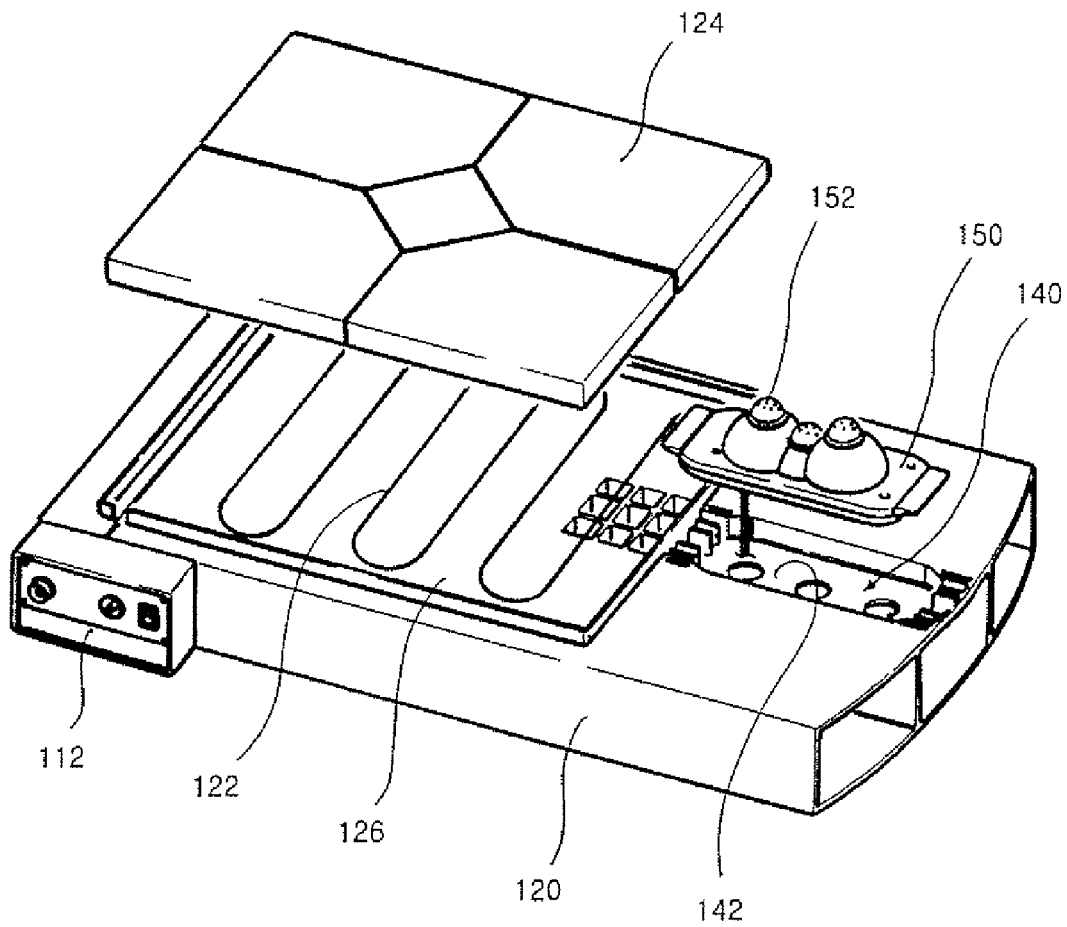
FIG. 3 is an exploded perspective view schematically illustrating essential components of the hyperthermo-therapeutic apparatus according to the present invention.

In the present invention, a space section 142 for receiving an external hyperthermo-therapeutic unit 150 is included in the receiving groove 140. The space section 142 may be formed as an open space section that is opened to the outside (see FIG. 2) or as a closed space section that is closed to the outside (see FIG. 3).

In the present invention, if the space section 142 is opened to the outside, there is an advantage in that upon engagement or separation of the external hyperthermo-therapeutic unit 150 with or from the receiving groove 140, it is possible to easily perform an engagement or separation operation by simply pushing the external hyperthermo-therapeutic unit 150 into or out of the receiving groove 140. On the contrary, if the space section 142 is closed to the outside, an operation for attaching or detaching the external hyperthermo-therapeutic unit 150 is somewhat troublesome, but there is an advantage in that the external hyperthermo-therapeutic unit 150 once mounted in the receiving groove 140 is maintained in a stable coupled state.

The hyperthermo-therapeutic apparatus 100 of the present invention comprises the external hyperthermo-therapeutic unit 150 that is detachably or slidably mounted in the receiving groove 140. In the present invention, the external hyperthermo-therapeutic unit 150 corresponds to the inner hyperthermo-therapeutic unit that is mounted and reciprocated in the mat, and is preferably one of so called a 3-member hyperthermo-therapeutic unit, a 4-member hyperthermo-therapeutic unit, a 6-member hyperthermo-therapeutic unit and a 9-member hyperthermo-therapeutic unit, which are known in the field of hyperthermo-therapeutic apparatuses.

In the present invention, the external hyperthermo-therapeutic unit 150 may be used while taking a conventional shape as it is or a new modified shape. If the external hyperthermo-therapeutic unit 150 is used while taking the conventional shape as it is, it is sufficient that the receiving groove 140 is formed to have a shape corresponding thereto. Thus, it is more preferred that the external hyperthermo-therapeutic unit 150 be used as it is without any modification. Further, since the conventional shape is utilized as it is without any modification in this case, there is an advantage in that if the external hyperthermo-therapeutic unit is not mounted in the receiving groove 140, the external hyperthermo-therapeutic unit can be used in a conventional manner. The external hyperthermo-therapeutic unit 150 basically comprises a hyperthermo-therapeutic member 152 for radiating far infrared rays when heat is applied thereto.

The hyperthermo-therapeutic apparatus 100 of the present invention comprises a hyperthermo-therapeutic unit cover 160 coupled above the external hyperthermo-therapeutic unit 150. The hyperthermo-therapeutic unit cover 160 has exposure opening(s) 162 through which the hyperthermo-therapeutic member 152 of the external hyperthermo-therapeutic unit 150 is exposed to the outside. The shape and number of the exposure opening(s) 162 are specifically determined according to the shape and number of the hyperthermo-therapeutic member(s) 152 of the external hyperthermo-therapeutic unit 150.

Figure 6A:
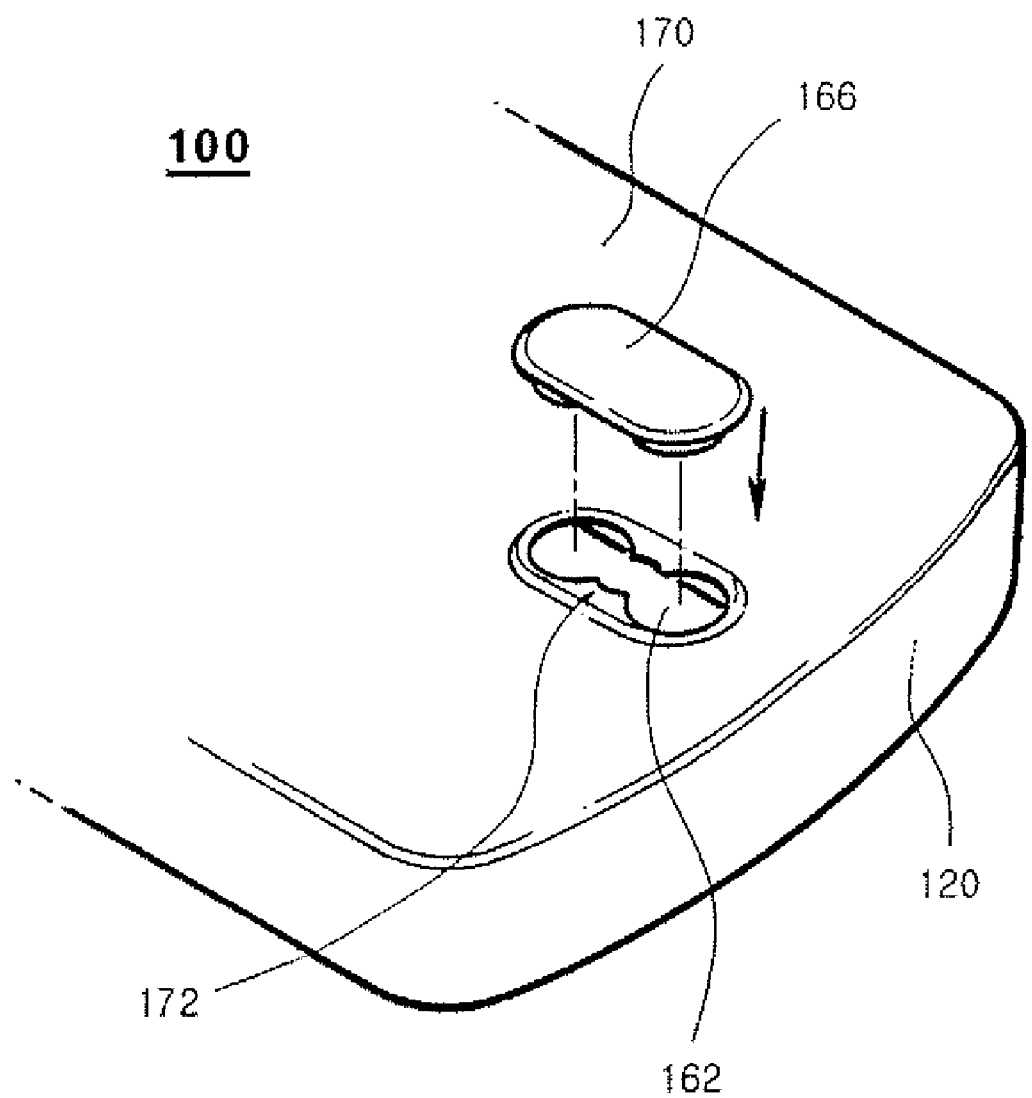
FIGS. 6A and 6B are exemplified views schematically showing a state where the hyperthermo-therapeutic apparatus 100 of the present invention is not utilized but safe-kept.
Figure 6B:
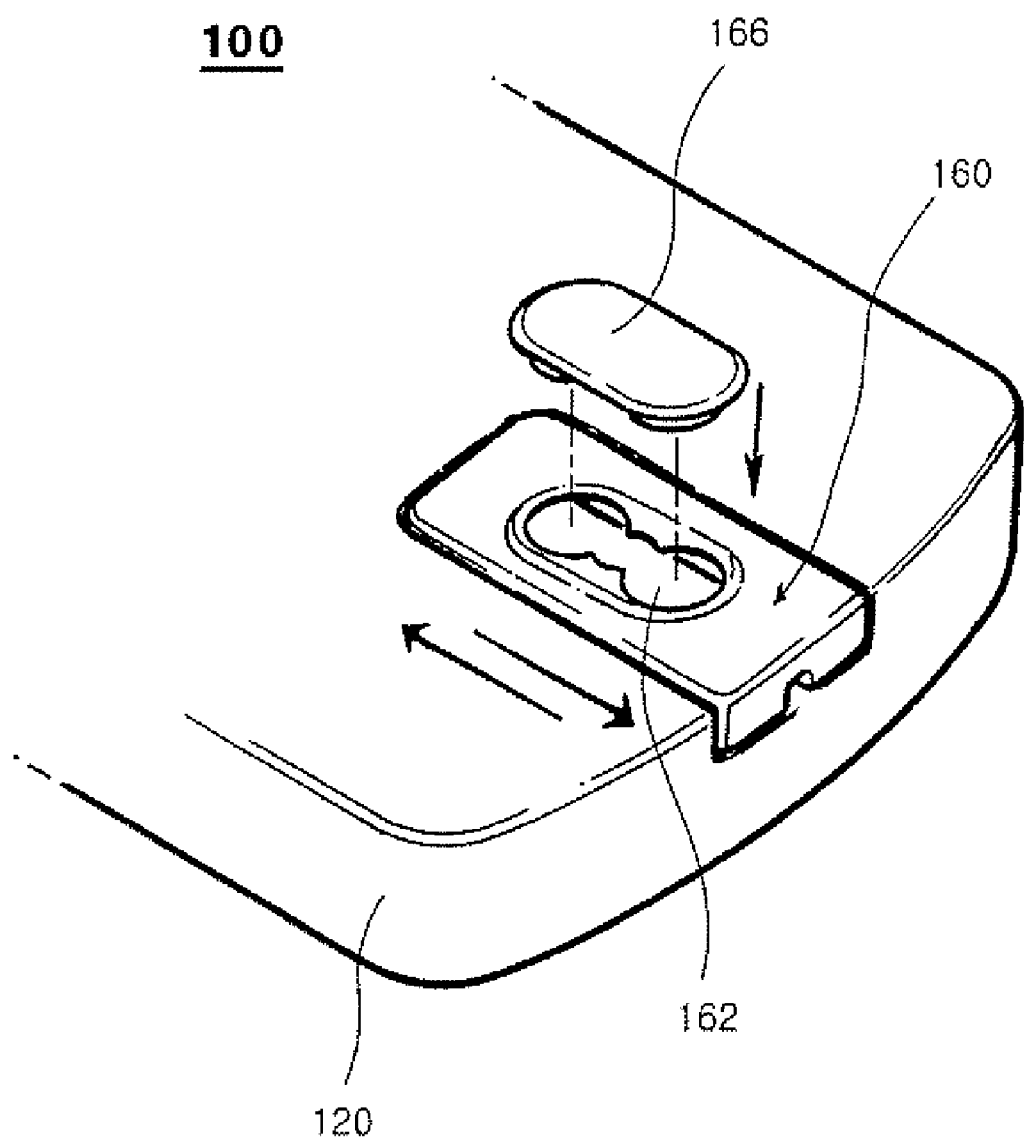

In the present invention, FIGS. 6A and 6B exemplarily show the shape of the exposure opening 162 that is suitable for the 3-member hyperthermo-therapeutic unit.

In the hyperthermo-therapeutic apparatus 100 of the present invention, it is preferred that the main mat 110 or the auxiliary mat 120 comprise a cover 170 for wrapping the body thereof. In the present invention, the cover 170 may wrap not only the main mat 110 and the auxiliary mat 120 but also the receiving groove 140 formed at a side of one of the mats and the external hyperthermo-therapeutic unit 150 engaged with the receiving groove 140. However, it is preferred that the cover 170 have an exposure opening 172 through which the hyperthermo-therapeutic member 152 of the external hyperthermo-therapeutic unit 150 is exposed to the outside. At this time, the exposure opening 172 is configured such that the exposure opening is coincident with the exposure opening 162 of the hyperthermo-therapeutic unit cover 160 when the cover 170 wraps the mats. This provides a foundation by which a user can easily utilize the hyperthermo-therapeutic apparatus 100.

It is preferred that the hyperthermo-therapeutic apparatus 100 of the present invention comprise a heat-generating means 122 provided in the auxiliary mat 120. In the present invention, the heat-generating means 122 is preferably provided inside with respect to the receiving groove 140. When the user lies on the main mat 110, a lower part of the user's body, i.e., the calf portion of the leg including a portion below the thigh corresponds to the heat-generating means, so that an intensive hot compress effect and an effect obtained by radiating far infrared rays can be provided to this portion. This enables further extension of the function of a conventional hyperthermo-therapeutic apparatus, since a hot compress effect and an effect obtained by radiating far infrared rays cannot be provided to the user's calf portion including the portion below the thigh in the conventional hyperthermo-therapeutic apparatus. The heat-generating means 122 preferably generates heat by using externally supplied electric energy. More specifically, the amount of the supplied electric energy and time during which the electric energy is supplied are controlled by an external control box 112.

In the present invention, it is more preferred that the heat-generating means 122 comprise a reflective sheet 126 placed at a lower portion thereof.

The hyperthermo-therapeutic apparatus 100 of the present invention preferably comprises a precious stone plate 124 placed on the heat-generating means 122. It is desirable to cut a natural ore into a thin sheet type precious stone plate 124. When the precious stone plate 124 is heated by the underlying heat-generating means 122, the precious stone plate radiates far infrared rays in an upward direction.

In the present invention, although the precious stone plate 124 may be manufactured and used as a single plate, it is more preferred that in view of convenience of machining and a crack generated upon use of the apparatus, the precious stone plate be formed of several platelets combined with one another. In the drawings of the present invention, there is exemplarily shown a precious stone plate formed of five platelets combined with one another.

The hyperthermo-therapeutic apparatus 100 of the present invention can be utilized in the following manner.

The present invention provides a method of using the hyperthermo-therapeutic apparatus 100 comprising the main mat 110 for mainly giving a hot compress effect to an upper part of a user's body and the auxiliary mat 120 for mainly giving a hot compress effect to a lower part of the user's body.

It is more preferred that the present invention be used in the form of a bed type hyperthermo-therapeutic apparatus comprising the main mat 110, the auxiliary mat 120 and the frame body 130 on which these mats are mounted.

The method of using the hyperthermo-therapeutic apparatus 100 according to the present invention comprises the step of mounting the external hyperthermo-therapeutic unit 150 in the receiving groove 140 formed at a side of the auxiliary mat 120.

First of all, a user grasps the external hyperthermo-therapeutic unit 150 and fits it into the receiving groove 140. At this time, if the receiving groove 140 is the open type, the user pushes the external hyperthermo-therapeutic unit 150 through an open side of the receiving groove 140 to mount the external hyperthermo-therapeutic unit. On the other hand, if the receiving groove 140 is the closed type, it is sufficient for the user to press down the external hyperthermo-therapeutic unit so that it can be mounted in the receiving groove.

Then, the external hyperthermo-therapeutic unit 150 is covered with the hyperthermo-therapeutic unit cover 160 so that the hyperthermo-therapeutic member 152 of the external hyperthermo-therapeutic unit 150 slightly protrudes outwardly through the exposure opening 162 of the hyperthermo-therapeutic unit cover. In this state, once the external hyperthermo-therapeutic unit 150 and the hyperthermo-therapeutic unit cover 160 are completely coupled with each other, the body of the external hyperthermo-therapeutic unit 150 is concealed and the hyperthermo-therapeutic member 152 of the external hyperthermo-therapeutic unit is exposed to the outside through the exposure opening 162 of the hyperthermo-therapeutic unit cover 160.

Although the hyperthermo-therapeutic unit cover 160 may be used to cover the external hyperthermo-therapeutic unit 150 thereabove in the present invention, it is not necessarily limited thereto. It is also possible to gently put the hyperthermo-therapeutic unit cover 160 directly on the external hyperthermo-therapeutic unit 150.

Figure 4:
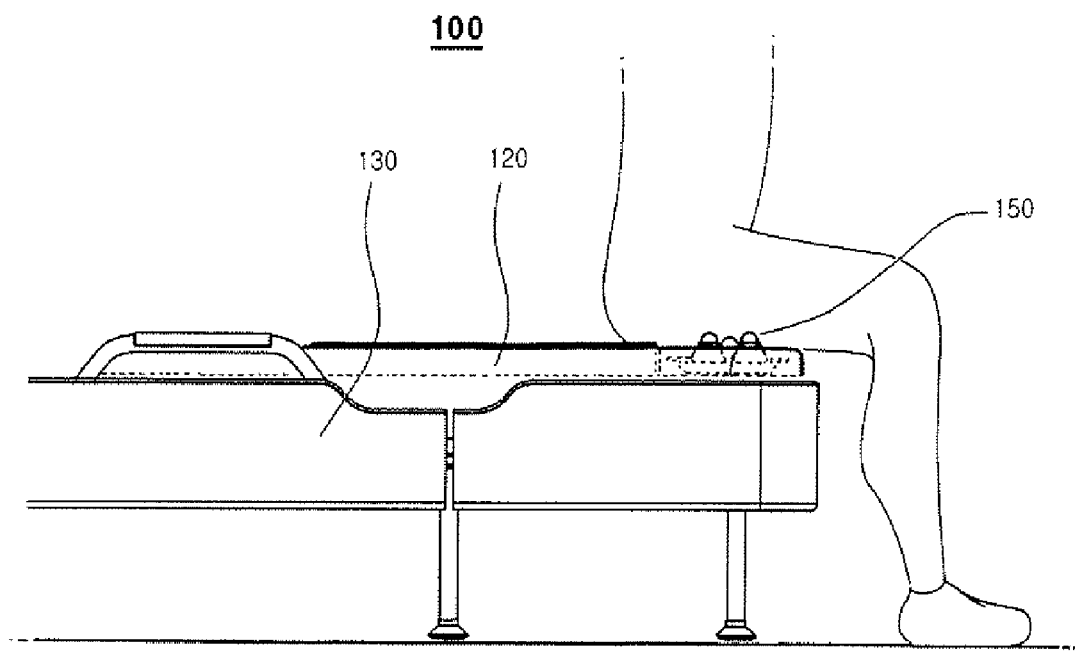
FIG. 4 is a schematic view exemplarily showing a use state where a user actually utilizes the hyperthermo-therapeutic apparatus 100 of the present invention, wherein the hyperthermo-therapeutic apparatus is constructed as a bed type hyperthermo-therapeutic apparatus.

The method of using the hyperthermo-therapeutic apparatus 100 according to the present invention comprises the step of sitting astraddle, by the user, on an upper side of the external hyperthermo-therapeutic unit 150 that has been mounted on the auxiliary mat 120. FIG. 4 exemplarily shows this step.

In the present invention, the external hyperthermo-therapeutic unit 150 is mounted safely in the receiving groove 140 of the auxiliary mat 120. In this state, only a plurality of hyperthermo-therapeutic members 152 slightly protrude upward, and the flat surface of the hyperthermo-therapeutic cover 160 around the hyperthermo-therapeutic members is flush with the surface of the main or auxiliary mat. Accordingly, if the user sits on a mounting portion of the receiving groove 140 of the auxiliary mat, the user can sit directly on hyperthermo-therapeutic members 152 of the external hyperthermo-therapeutic unit 150 mounted in the receiving groove 140. At this time, if the hyperthermo-therapeutic apparatus 100 is the bed type, the figure of the user sitting on the auxiliary mat is identical with that of one who commonly sits on a chair or sofa. Thus, the figure of the user appears to be natural and comfortable. Further, if the hyperthermo-therapeutic apparatus 100 is the mat type, the figure of the user is identical with that of one who sits on a mat or cushion. Thus, the user can take a very comfortable posture. Since this posture appears to be a very natural figure, the user does not need to be particularly conscious of people around the user.

In addition, the method of using the hyperthermo-therapeutic apparatus 100 according to the present invention comprises the step of operating the external hyperthermo-therapeutic unit 150 to obtain a hot compress effect and an effect generated by radiating far infrared rays.

In the present invention, since the external hyperthermo-therapeutic unit 150 may be a conventional one that has been commonly used, it is sufficient to operate it in a conventional manner. For example, operating time and temperature of the external hyperthermo-therapeutic unit can be adjusted by manipulating a remote control 15. However, since such an operating manner is merely an ordinary manner, a detailed description thereof will be omitted herein.

Meanwhile, although the foregoing has been described in connection with the case where the user mounts the external hyperthermo-therapeutic unit 150 in the receiving groove 140 and then operates the external hyperthermo-therapeutic unit 150, this is only to describe the preferred embodiment of the present invention. The technical spirit of the present invention can be implemented even in a case where the external hyperthermo-therapeutic unit 150 can be first operated and then mounted and used in the receiving groove 140.

After use of the hyperthermo-therapeutic apparatus 100 of the present invention, it is desirable to store the hyperthermo-therapeutic apparatus as follows.

FIGS. 6A and 6B are exemplified views schematically showing a state where the hyperthermo-therapeutic apparatus 100 of the present invention is not utilized but safe-kept. As shown in FIGS. 6A and 6B, it is preferred that the user separate the external hyperthermo-therapeutic unit 150, mount the hyperthermo-therapeutic unit cover 160 in that place and then put a lid 166 thereon. The lid 166 is preferably formed to be engaged with the exposure opening 162.

INDUSTRIAL APPLICABILITY

The present invention relates to an auxiliary mat for a hyperthermo-therapeutic apparatus and a hyperthermo-therapeutic apparatus comprising the same, wherein a user can more effectively obtain a hot compress effect and an effect generated by radiating far infrared rays on a crotch region of a lower part of the user's body.

Although the bed type hyperthermo-therapeutic apparatus according to the present invention has been specifically described above, it is intended to illustrate the most preferred embodiment of the present invention. The present invention is not limited thereto and the scope of the invention is determined and defined only by the appended claims.

Further, it will be apparent that those skilled in the art can make various changes and modifications thereto from the disclosure herein, and the various changes and modifications fall within the scope of the invention.

The invention claimed is:

1. An auxiliary mat for a hyperthermo-therapeutic apparatus, comprising:
   a receiving groove formed at a side of a body of the mat;
   an external hyperthermo-therapeutic unit detachably mounted in the receiving groove; and
   a hyperthermo-therapeutic unit cover coupled above the external hyperthermo-therapeutic unit while outwardly exposing a hyperthermo-therapeutic member of the external hyperthermo-therapeutic unit.

2. The auxiliary mat as claimed in claim 1, wherein the external hyperthermo-therapeutic unit is slidably mounted in the receiving groove.

3. The auxiliary mat as claimed in claim 1, wherein the receiving groove has an external side opening provided in a side wall of the auxiliary mat such that the external hyperthermo-therapeutic unit can be slidably inserted into the receiving groove as the external hyperthermo-therapeutic unit engages a bottom of the receiving groove.

4. The auxiliary mat as claimed in claim 1, wherein the hyperthermo-therapeutic unit cover has a shape corresponding to the receiving groove.

5. The auxiliary mat as claimed in claim 1, further comprising a lid that detachably covers an exposure opening of the hyperthermo-therapeutic unit cover, the exposure opening exposing a hyperthermo-therapeutic member of the external hyperthermo-therapeutic unit to an outside of the hyperthermo-therapeutic unit cover.

6. A hyperthermo-therapeutic apparatus including a main mat for use in giving a hot compress effect to an upper part of a user's body and an auxiliary mat for use in giving a hot compress effect to a lower part of the user's body, the auxiliary mat further comprising:
   a receiving groove formed at a side of a body of the auxiliary mat;
   an external hyperthermo-therapeutic unit detachably mounted in the receiving groove; and
   a hyperthermo-therapeutic unit cover coupled above the external hyperthermo-therapeutic unit while outwardly exposing a hyperthermo-therapeutic member of the external hyperthermo-therapeutic unit.

7. The apparatus as claimed in claim 6, wherein the external hyperthermo-therapeutic unit is slidably mounted in the receiving groove of the auxiliary mat.

8. The apparatus as claimed in claim 6, wherein the hyperthermo-therapeutic unit cover coupled with the auxiliary mat comprises an exposure opening through which the hyperthermo-therapeutic member of the external hyperthermo-therapeutic unit is exposed to the outside.

9. The apparatus as claimed in claim 6, wherein the receiving groove has an external side opening provided in a side wall of the auxiliary mat such that the external hyperthermo-therapeutic unit can be slidably inserted into the receiving groove as the external hyperthermo-therapeutic unit engages a bottom of the receiving groove.

10. The apparatus as claimed in claim 6, wherein the hyperthermo-therapeutic unit cover has a shape corresponding to the receiving groove.

11. The apparatus as claimed in claim 6, further comprising a lid that detachably covers an exposure opening of the hyperthermo-therapeutic unit cover, the exposure opening exposing a hyperthermo-therapeutic member of the external hyperthermo-therapeutic unit to an outside of the hyperthermo-therapeutic unit cover.

12. The apparatus as claimed in claim 7, wherein the hyperthermo-therapeutic unit cover coupled with the auxiliary mat comprises an exposure opening through which the hyperthermo-therapeutic member of the external hyperthermo-therapeutic unit is exposed to the outside.

13. The apparatus as claimed in claim 6, wherein when the external hyperthermo-therapeutic unit and the hyperthermo-therapeutic unit cover are completely coupled with each other at the side of the auxiliary mat, a body of the external hyperthermo-therapeutic unit is concealed and the hyperthermo-therapeutic member of the external hyperthermo-therapeutic unit is exposed to the outside through the exposure opening of the hyperthermo-therapeutic unit cover.

14. The apparatus as claimed in claim 13, wherein the auxiliary mat further comprises a heat generator that generates heat by using externally supplied electric energy; and a precious stone plate lying on the heat generator and radiating far infrared rays by the heat generated by the heat generator.

15. The apparatus as claimed in claim 14, wherein the precious stone plate comprises a plurality of platelets.

16. The apparatus as claimed in claim 14, wherein the auxiliary mat and the main mat coupled therewith are mounted on a frame body.

17. A method of using a hyperthermo-therapeutic apparatus including a main mat for use in giving a hot compress effect to an upper part of a user's body and an auxiliary mat for use in giving a hot compress effect to a lower part of the user's body, comprising:
   mounting, by a user, an external hyperthermo-therapeutic unit in a receiving groove formed at a side of the auxiliary mat;
   sitting astraddle, by the user, on an upper side of the external hyperthermo-therapeutic unit mounted in the receiving groove; and
   operating, by the user, the external hyperthermo-therapeutic unit to obtain a hot compress effect.

18. The method as claimed in claim 17, further comprising:
   generating heat, by a heat generator mounted in the auxiliary mat, using externally supplied electric energy; and
   radiating far infrared rays by a precious stone plate lying on the heat generator using the heat from the heat generator.

19. The method as claimed in claim 18, wherein the auxiliary mat and the main mat coupled therewith are mounted on a frame body.

* * * * *